United States Patent [19]

Meyer

[11] Patent Number: 4,759,792
[45] Date of Patent: Jul. 26, 1988

[54] PHENYLSULFONYLUREAS

[75] Inventor: Willy Meyer, Riehen, Switzerland

[73] Assignee: Ciba-Geigy Corporation, Ardsley, N.Y.

[21] Appl. No.: 53,915

[22] Filed: May 26, 1987

[30] Foreign Application Priority Data

Jun. 5, 1986 [CH] Switzerland .................. 2291/86

[51] Int. Cl.$^4$ ............... A01N 43/54; C07D 239/69
[52] U.S. Cl. ............................ 71/92; 544/321; 544/323; 544/332
[58] Field of Search ............. 71/92; 544/321, 323, 544/332

[56] References Cited

U.S. PATENT DOCUMENTS

| | | | |
|---|---|---|---|
| 4,425,154 | 1/1984 | Meyer et al. | 71/92 |
| 4,443,243 | 4/1984 | Fory et al. | 71/93 |
| 4,523,944 | 6/1985 | Föry et al. | 71/92 |
| 4,579,584 | 4/1986 | Meyer et al. | 71/93 |
| 4,618,363 | 10/1986 | Gass et al. | 71/92 |
| 4,634,465 | 1/1987 | Ehrenfreund et al. | 71/91 |

FOREIGN PATENT DOCUMENTS 107979 5/1984 European Pat. Off. .

Primary Examiner—John M. Ford
Attorney, Agent, or Firm—Kevin T. Mansfield; Edward McC. Roberts

[57] ABSTRACT

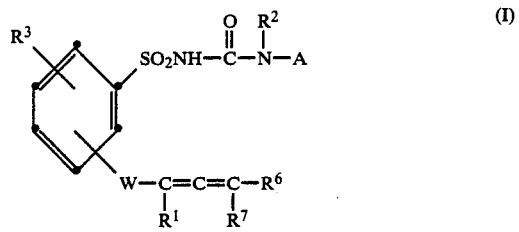

and the salts of these compounds with amines, alkali or alkali earth metal bases or with quaternary ammonium bases have good pre- and post-emergence, selective herbicidal and growth-regulating properties. In this formula $R^1$ and $R^2$, independently of each other, are hydrogen or $C_1$-$C_2$alkyl, $R^3$ is hydrogen, halogen, nitro, $C_1C_4$alkyl, $C_1$-$C_4$-Haloalkyl, $C_1$-$C_4$-alkoxy, $C_1$-$C_4$haloalkoxy, $C_1$-$C_4$alkoxycarbonyl, $C_1$-$C_4$alkylthio, $C_1$-$C_4$alkylsulfinyl, $C_1$-$C_4$alkylsulfonyl or $C_2$-$C_5$alkoxyalkoxy or —$SO_2NR^4R^5$, $R^4$ is hydrogen, $C_1$-$C_2$alkoxy or $C_1$-$C_4$alkyl, $R^5$ is hydrogen, methyl or ethyl, $R^6$ and $R^7$ are each hydrogen, methyl or ethyl, W is oxygen, sulfur, a sulfinyl and sulfonyl bridge A is a radical selected from

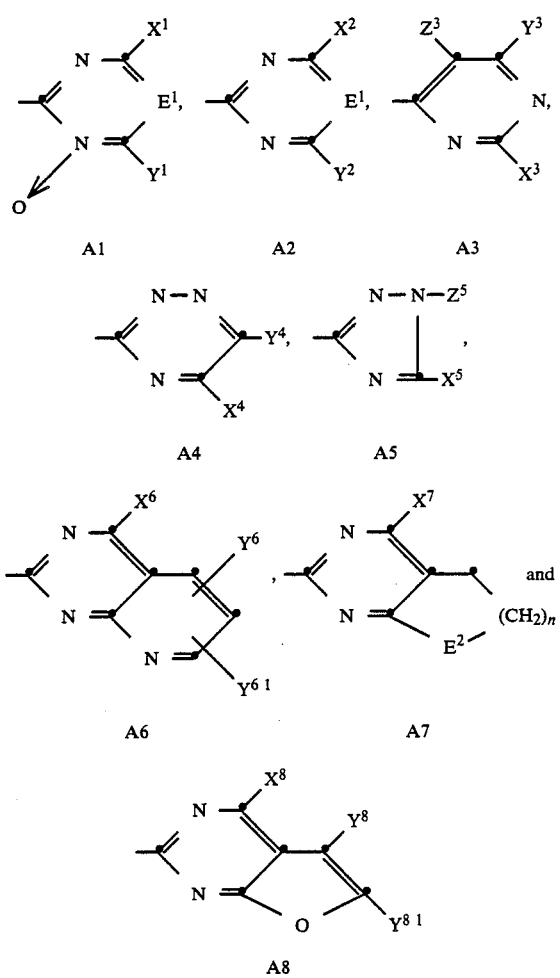

in which the substituents $E^1$, $E^2$, $X^1$, $X^2$, $X^3$, $X^4$, $X^5$, $X^6$, $X^7$, $X^8$, $Y^1$, $Y^2$, $Y^3$, $Y^4$, $Y^6$, $Y^{61}$, $Y^8$, $Y^{81}$, $Z^3$ and $Z^5$ are customary organic radicals.

10 Claims, No Drawings

PHENYLSULFONYLUREAS

The present invention relates to novel phenylsulfonylureas, in particular N-phenylsulfonyl-N'-pyrimidinyl-, N'-triazolyl- or N'-triazinyl ureas with herbicidal and plant growth regulating properties, to the preparation thereof, to compositions containing them as active ingredient, and to their use for controlling weeds, especially for selective weed control in crops of useful plants, or for the regulation and inhibition of plant growth.

The compounds of the invention have the formula I

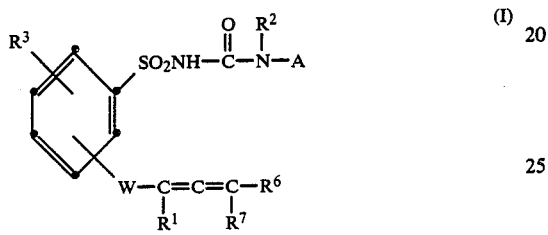

wherein $R^1$ and $R^2$, independently of each other, are hydrogen or $C_1$-$C_2$alkyl, $R^3$ is hydrogen, halogen, nitro, $C_1C_4$alkyl, $C_1$-$C_4$haloalkyl, $C_1$-$C_4$-alkoxy, $C_1$-$C_4$haloalkoxy, $C_1$-$C_4$alkoxycarbonyl, $C_1$-$C_4$alkylthio, $C_1$-$C_4$alkylsulfinyl, $C_1$-$C_4$alkylsulfonyl or $C_2$-$C_5$alkoxyalkoxy or —$SO_2NR^4R^5$, $R^4$ is hydrogen, $C_1$-$C_2$alkoxy or $C_1$-$C_4$alkyl, $R^5$ is hydrogen, methyl or ethyl, $R^6$ and $R^7$ are each hydrogen, methyl or ethyl, W is oxygen, sulfur, a sulfinyl and sulfonyl bridge A is a radical

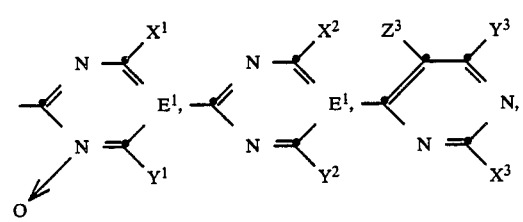

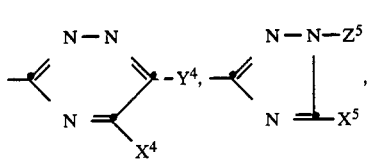

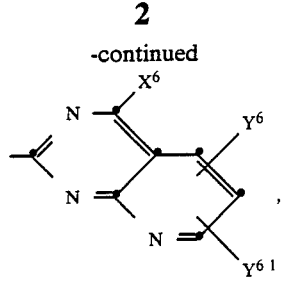

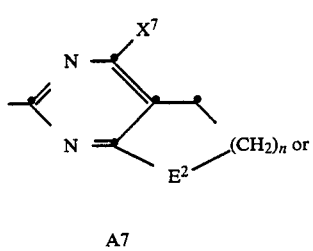

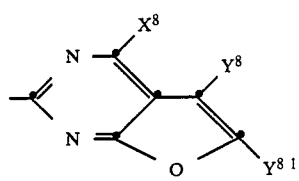

$X^1$, $X^2$, $X^3$, $X^4$, $X^5$, $X^6$, $X^7$, $X^8$ and $Y^1$ are each independently halogen, $C_1$-$C_4$haloalkoxy, $C_1$-$C_4$haloalkyl, $C_1$-$C_4$alkoxy, $C_1$-$C_4$alkyl, dimethylamino, methylamino, ethylamino, amino or $C_2$-$C_4$alkoxyalkyl, $E^1$ is nitrogen or the methine bridge, $E^2$ is oxygen or the methylene bridge, $Y^2$ has the same meaning as $Y^1$ or is cyclopropyl, dimethoxymethyl, diethoxymethyl

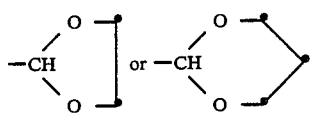

$Y^3$ is methyl, methoxy, ethyl, ethoxy, $C_1$-$C_2$haloalkyl or $C_1$-$C_2$haloalkoxy, $Y^4$ is hydrogen, methoxy, ethoxy, halogen or $C_1$-$C_4$alkyl, $Y^6$ and $Y^{61}$, independently of each other, are hydrogen, $C_1$-$C_4$alkyl, halogen, methoxy or methylthio, $Y^8$ and $Y^{81}$, independently of each other, are hydrogen or methyl, n is 1 or 2, $Z^3$ is hydrogen, methyl, ethyl, methoxy, ethoxy, methoxycarbonyl, ethoxycarbonyl, halogen, cyan, nitro, methylthio, methylsulfinyl or methylsulfonyl, $Z^3$ and $Y^3$ together are a $C_2$-$C_4$alkylene bridge, and $Z^5$ is methyl or ethyl.

Herbicidal urea, triazine and pyrimidine compounds are generally known. Sulfonylureas having herbicidal and plant growth regulating properties have recently been described, e.g. in published European patent applications 99339 and 107979.

In the above definitions, alkyl will be understood as meaning linear or branched alkyl; e.g. methyl, ethyl, n-propyl, isopropyl or the four isomers of butyl.

Alkoxy will be understood as: methoxy, ethoxy, n-propyloxy, isopropoxy or the four butyloxy isomers with methoxy, ethoxy or isopropoxy being preferred.

Alkylthio may be methylthio, ethylthio, n-propylthio, isopropylthio or the four butylthio isomers, with methylthio and ethylthio being preferred.

Halogen itself and as moiety of a substituent as in haloalkoxy, haloalkylthio or haloalkyl will be understood as meaning fluorine, chlorine and bromine, preferably fluorine and chlorine. Haloalkyl by itself or as moiety of haloalkoxy or haloalkylthio is usually chloromethyl, fluoromethyl, difluoromethyl, trifluoromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3- trifluoropropyl, 2,3-dichloropropyl, 1,1,2,3,3,3-hexafluoropropyl, preferably fluoromethyl, chloromethyl, difluoromethyl and trifluoromethyl.

Examples of alkoxyalkyl are: methoxymethyl, methoxyethyl, methoxypropyl, ethoxyethyl, ethoxymethyl or propyloxymethyl. Examples of alkoxyalkoxy include: methoxymethoxy, methoxyethoxy, methoxypropyloxy, ethoxymethoxy, ethoxyethoxy and propyloxymethoxy. Alkylene groups are defined under formula I as ethylene, propylene, butylene, 1-methylethylene, 1-ethylethylene, 2-methylbutylene, 1-methylbutylene or, if the bridge is interrupted by oxygen, —CH$_2$—O—CH$_2$— or —CH$_2$—O—CH$_2$—CH$_2$—.

The invention also encompasses the salts which the compounds of formula I can form with amines, alkali metal bases and alkaline earth metal bases or quaternary ammonium bases.

The salt-forming alkali metal and alkaline earth metal hydroxides include the hydroxides of lithium, sodium, potassium, magnesium and calcium, but preferably those of sodium and potassium.

Amines suitable for forming salts include primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine-di-n-butylamine, pyrrolidine, piperidine, morpholine, trimethylamine, triethylamine, tripropylamine, quinuclidine, pyridine, quinoline and isoquinoline, but preferably ethylamine, propylamine, diethylamine and triethylamine, most preferably isopropylamine, diethanolamine and 1,4-diazabicyclo(2.2.-2)octane.

Examples of quaternary ammonium bases are in general the cations of haloammonium salts, e.g., the tetramethylammonium cation, the tetraethylammonium cation, the trimethylethylammonium cation, but also the ammonium cation. Among the compounds of formula I preference is given to those in which the radical

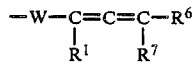

is in position 2 and A either a pyrimidine radical of the formula

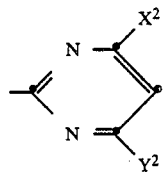

in which $X^2$ and $Y^2$ have the significance given in formula I, in particular those in which $R^1$, $R^2$, $R^3$, $R^6$ and $R^7$ represent hydrogen; especially N-(2-allenyloxyphenylsulfonyl)-N'(4-methoxy-6-methylpyrimidin-2-yl)-urea and N-(2-allenyloxyphenylsulfonyl)-N'-(4,6-dimethoxypyrimidin-2yl)-urea.

N-(2-allenyloxyphenylsulfonyl)-N'-[4,6-bis-(difluormethoxy)-pyrimidin-2-yl]-urea, or a triazinyl radical of the formula

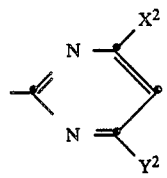

in which $X^2$ and $Y^2$ are as defined for formula I, in particular those in which $R^1$, $R^2$ and $R^3$ represent hydrogen, most preferably N-(2-allenyloxyphenylsulfonyl)-N'-(4-methoxy-6-methyl-1,3,5,-triazin-2-yl)-urea.

The compounds of formula I are in general prepared according to the following methods:

One process for preparing the compounds of formula I comprises reacting an allenyloxysulfonamide of formula II

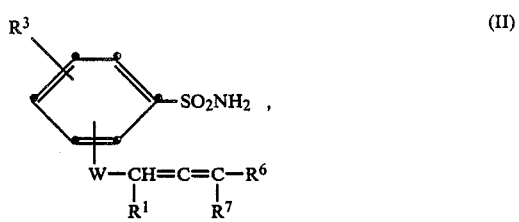

in which $R^1$, $R^3$, $R^6$, $R^7$ and W are as defined for formula I, with a carbamate of formula III

in which $R^2$, A and W are as defined for formula I and R is phenyl, alkyl or substituted phenyl in the presence of a base.

A second process for preparing compounds of formula I comprises reacting a sulfonyl carbamate of the formula IV

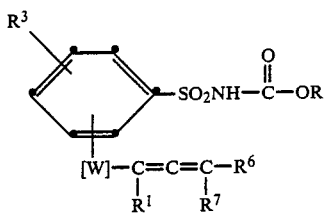

(IV)

in which $R^1$, $R^3$, $R^6$, $R^7$ and W are as defined for formula I and R is phenyl, alkyl or substituted phenyl, with an amine of formula V

(V)

in which A and $R^2$ are as defined for formula I.

Finally, the compounds of formula I can be obtained by reacting a sulfonamide of the above formula II with an isocyanate of formula VI

OCN—A  VI in which A has one of the meanings given under formula I.

If desired, the compounds of formula I can be converted into addition salts by means of amines, alkali metal or alkaline earth metal hydroxides, or quaternary ammonium bases. This is effected, for example, by reacting the compounds of formula I with the equimolar amount of base and evaporating the solvent. The reactions to obtain the compounds of formula I are conveniently carried out in aprotic, inert organic solvents. Such solvents include hydrocarbons such as benzene, toluene, xylene or cyclohexane, tetrachlorocarbon or chlorobenzene, ethers such as diethylether, ethylene glycol dimethyl ether, diethylene glycol dimethylether, tetrahydrofuran or dioxane, nitriles such as acetonitrile or propionitrile, amides such as dimethylformamide, diethylformamide or N-methylpyrrolidinone. The reaction temperatures are preferably in the range from −20° to +120° C. The reactions in the coupling processes are generally slightly exothermic and can be carried out at room temperature. To shorten the reaction time or to induce the conversion, it is convenient to heat the reaction mixture briefly to boiling point. The reaction times can also be shortened by adding a few drops of base as reaction catalyst. Particularly suitable bases include tertiary amines such as trimethylamine, triethylamine, quinuclidine, 1,4-diazabicyclo(2.2.2)-octane, 1,5-diazabicyclo-(4.3.0)non-5-ene or 1,8-diazabicyclo(5.4.-0)undec-7-ene. Inorganic bases such as hydrides, e.g. sodium or calcium hydride, hydroxides such as sodium and potassium hydroxide, carbonates such as sodium and potassium carbonate, or hydrogen carbonates such as potassium and sodium hydrogen carbonate, may be used as bases.

The final products of formula I can be isolated by concentration and/or evaporation of the solvent, and purified by recrystallising or grinding the solid residue in solvents in which they are poorly soluble, such as ethers, aromatic hydrocarbons or chlorinated hydrocarbons.

The allenyloxy- and allenylthiophenylsulfonamide of formula II required as an intermediate can be prepared by one of the following methods:

A propinyloxy or thiophenylsulfonamide is stirred in an inert organic solvent in the presence of potassium-tert-butylate at a temperature of 0°-50° C. until the propinyl-allene rearrangement has taken place.

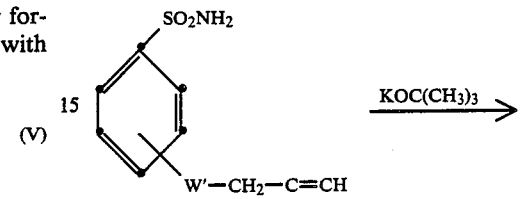

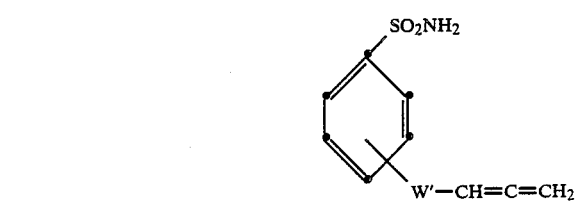

2-chlorallyloxy or thiophenylsulfonamide can be similarly converted in the presence of potassium-tert-butylate to allenyloxyphenylsulfonamide.

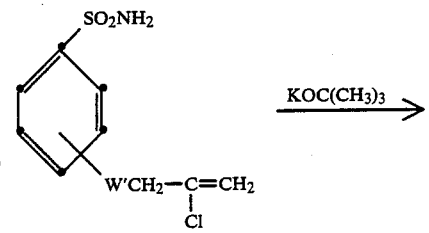

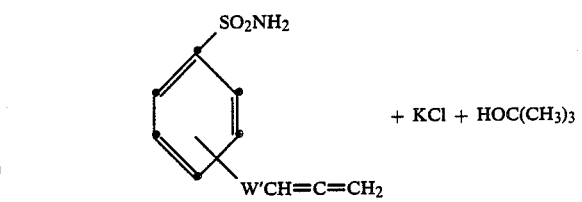

W' = oxygen or sulfur

The conversions or rearrangements take place at low temperature of 0°-50° C. in an inert organic solvent such as dimethylsulfoxide, dimethylformamide, dioxane, cellosolve, dipropylether, ethanol or tetrahydrofuran. On termination of the reaction, the reaction mixture is neutralised with dilute aqueous mineral acid and the allene isolated by extraction therefrom.

Sulfoxides and sulfones of the allenylthiosulfonamides are obtained by oxidation with hydrogen peroxide in an organic solvent such as acetic acid according to the following reaction scheme:

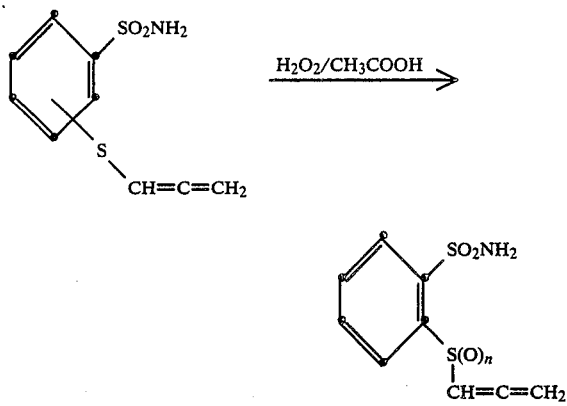

The intermediates of formula IV are obtained by known methods from the allenyloxyphenylsulfonamide of formula II. The starting materials used are aminopyrimidines, aminotriazoles and aminotriazines of formula V as well as appropriate carbamates of formula III, and are either known or can be obtained by known methods that are described in the literature. The active ingredients of formula I are stable compounds. Their handling requires no special precautionary measures.

When used at low rates of application, the compounds of formula I have good selective growth inhibiting and selective herbicidal properties which make them most suitable for use in crops of useful plants, preferably in cereals, cotton, soybeans, maize and rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of formula I are effective even when used at very low rates of application.

The compounds of formula I have in addition pronounced plant growth inhibiting properties. The growth of both monocots and dicots is inhibited.

Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth inhibitors resides in the fact that nutrients are able increasingly to promote flower formation and fruiting, whereas vegetative growth is inhibited.

The compounds of formula I can also be used for defoliating and desiccating crops of cotton and potatoes. By treating the crops at the moment of ripening, the harvesting of the cotton capsules or of the tubers is greatly facilitated when the leaves fall off and/or shrivel up or when the shrubs shrivel up.

At higher rates of application of compounds of formula I, all tested plants are so severely damaged in their development that they die.

The invention also relates to herbicidal and plant growth regulating compositions which contain a novel compound of formula I, and also to methods of controlling weeds pre- and postemergence and of inhibiting the growth of monocots and dicots, especially grasses, tropical cover crops and tobacco plant suckers.

The compounds of formula I are used in unmodified form or, preferably, together with the adjuvants conventionally employed in the art of formulation, and are therefore formulated in known manner e.g. to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch" (Handbook of Surfactants), C. Hanser Verlag, Munich & Vienna, 1981.

The pesticidal preparations usually contain 0.1 to 95%, preferably 0.1 to 80%, of a compound of formula I, 1 to 99.9% of a solid or liquid adjuvant, and 0 to 25%, preferably 0.1 to 25%, of a surfactant.

Preferred formulations are composed in particular of the following constituents (%=percentage by weight):

| Emulsifiable concentrates | | |
|---|---|---|
| compound of formula I: | 1 to 20%, | preferably 5 to 10% |
| surfactant: | 5 to 30%, | preferably 10 to 20% |
| liquid carrier: | 50 to 94%, | preferably 70 to 85% |
| Dusts | | |
| compound of formula I: | 0.1 to 10%, | preferably 0.1 to 1% |
| solid carrier: | 99.9 to 90%, | preferably 99.9 to 99% |
| Suspension concentrates | | |
| compound of formula I: | 5 to 75%, | preferably 10 to 50% |
| water: | 94 to 25%, | preferably 90 to 30% |
| surfactant: | 1 to 40%, | preferably 2 to 30% |
| Wettable powders | | |
| compound of formula I: | 0.5 to 90%, | preferably 1 to 80% |
| surfactant: | 0.5 to 20%, | preferably 1 to 15% |
| solid carrier: | 5 to 95%, | preferably 15 to 90% |
| Granulates | | |
| compound of formula I: | 0.5 to 30%, | preferably 3 to 15% |
| solid carrier: | 99.5 to 70%, | preferably 97 to 85%. |

Whereas commercial products will be preferably formulated as concentrates, the end user will normally employ dilute formulations. The formulations can be diluted to a concentration as low as 0.001% of active ingredient. The rates of application are usually from 0.005 to 5 kg a.i./ha.

The compositions may also contain further ingredients such as stabilisers, antifoams, viscosity regulators, binders, tackifiers, as well as fertilisers and other compounds for obtaining special effects.

Preparatory Examples

Example 1

Preparation of N-(2-allenyloxyphenylsulfonyl)-N'-4,6-bis(difluoromethoxy-1,3-pyrimid-2-yl)urea

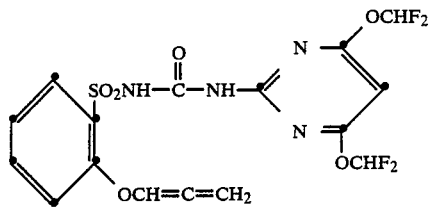

A solution of 1.52 g of 1,8-diazabicyclo[5.5.0]undec-7-ene (1.5-5) and 10 ml of methylene chloride is added dropwise to a mixture of 2.53 g of 4,6-bis(difluoromethoxy-1,3-pyrimid-2-ine) isocyanate, 2.11 g of 2-allenyloxyphenylsulfonamide and 70 ml of methylene chloride. The reaction mixture is stirred for 5 hours at room temperature and then evaporated to dryness. The residue is stirred in water, adjusted to pH 6 with dilute hydrochloric acid and extracted with ethyl acetate. The extract is washed with water, dried, and concentrated by evaporation. The residue is crystallised from ether, affording 0.65 g of the title compound with a melting point of 139°–140° C.

The starting 2-allenyloxyphenylsulfonamide is obtained as follows:

(a) 2-Allenyloxyphenylsulfonamide 4.5 g of potassium tert-butylate are added in portions to a solution of 5 g of 2-(2-chloroprop-2-enyloxy)-phenylsulfonamide such that the temperature does not exceed 28° C. The reaction mixture is stirred for 20 hours at 20°-25° C. and, after addition of ice-water, adjusted to pH 7 by the dropwise addition of 10% hydrochloric acid and extracted with ethyl acetate. The extract is washed with water and hydrochloric acid, dried over sodium sulfate and concentrated by evaporation. The residue is chromatographed through a column of silica gel to give pure 2-allenyloxyphenylsulfonamide of m.p. 94°-95° C.

This compound can also be prepared as follows:

(b) 2-Allenyloxyphenylsulfonamide 4.4 g of potassium tert-butylate are added in portions to a solution of 6.33 g of 2-propynyloxyphenylsulfonamide and 40 ml of dimethyl sulfoxide such that the temperature does not exceed 28° C. The reaction mixture is stirred for 4 hours at 20°-25° C. and, after addition of ice-water, adjusted to pH 7 by the dropwise addition of dilute hydrochloric acid and extracted with ethyl acetate. The organic phase is washed with water and brine, dried over sodium sulfate and concentrated by evaporation. The residue is chromatographed through a column of silica gel to give 1 g of 2-allenyloxyphenylsulfonamide of m.p. 94°-95° C.

Example 2

Preparation of N-(2-allenyloxyphenylsulfonyl)-N'-(4-methoxy-6-methyl-1,3,5-triazin-2-yl)urea

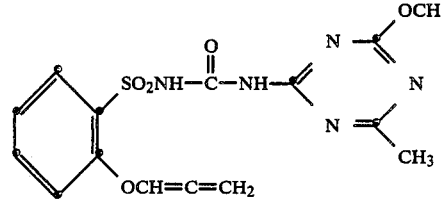

A mixture of 1.7 g of 2-allenyloxyphenylsulfonamide, 2.08 g of 4-methoxy-6-methyl-1,3,5-triazin-2-ylphenyl-carbamate, 1.22 g of 1,8-diazabicyclo[5.4.0]undec-7-ene (1.5-5) and 50 ml of absolute dioxane is stirred for 4 hours at 20°-25° C. The reaction mixture is poured into water and, after adjusting the pH 6 by the dropwise addition of 10% hydrochloric acid, extracted with ethyl acetate. The organic phase is dried and concentrated by evaporation. The residue is crystallised from ethyl acetate to give 1.8 g of the title compound of m.p. 150°-151° C. (dec).

TABLE 01

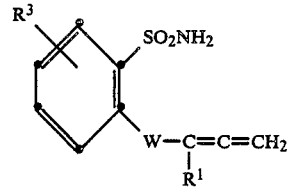

| Comp. No. | $R^1$ | $R^3$ | W | m.p. (°C.) |
|---|---|---|---|---|
| 01.01 | H | H | O | 94–95° C. |
| 01.02 | $CH_3$ | H | O | 110–111° C. |
| 01.03 | H | 5-$CH_3$ | O | |
| 01.04 | H | 5-Cl | O | |
| 01.05 | H | 5-F | O | |
| 01.06 | H | 6-Cl | O | |
| 01.07 | H | 6-$NO_2$ | O | |
| 01.08 | H | 3-Cl | O | |
| 01.09 | H | H | S | 119–120° C. |
| 01.10 | H | H | SO | |
| 01.11 | H | H | $SO_2$ | 169–70° C. |
| 01.12 | $CH_3$ | H | S | |
| 01.13 | $CH_3$ | H | SO | |
| 01.14 | $CH_3$ | H | $SO_2$ | |
| 0.015 | 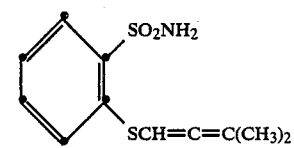 | | | 102–103° C. |

TABLE 02

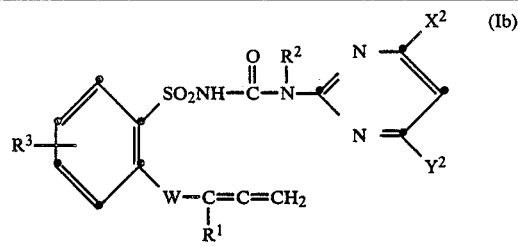

| Comp. No. | $R^1$ | $R^2$ | $R^3$ | W | $X^2$ | $Y^2$ | m.p. (°C.) |
|---|---|---|---|---|---|---|---|
| 02.01 | H | H | H | O | $CH_3$ | $CH_3$ | 179–180° C. |
| 02.02 | H | H | H | O | $CH_3$ | $C_2H_5$ | |
| 02.03 | H | H | H | O | $CH_3$ | $OCH_3$ | 145–146° C. |
| 02.04 | H | H | H | O | $CH_3$ | $OC_2H_5$ | |
| 02.05 | H | H | H | O | $CH_3$ | $OCHF_2$ | 157–158° C. dec. |
| 02.06 | H | H | H | O | $CH_3$ | $OCH_2CF_3$ | |
| 02.07 | H | H | H | O | $CH_3$ | 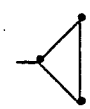 | |
| 02.08 | H | H | H | O | $CH_3$ | HN—$CH_3$ | |
| 02.09 | H | H | H | O | $CH_3$ | $N(CH_3)_2$ | |
| 02.10 | H | H | H | O | $CH_2Cl$ | $OCH_3$ | |
| 02.11 | H | H | H | O | $C_2H_5$ | $OCH_3$ | |
| 02.12 | H | H | H | O | $C_2H_5$ | $OCHF_2$ | |

TABLE 02-continued

Structure (Ib): Phenyl ring with R³ substituent, SO₂NH-C(=O)-N(R²)- connected to a pyrimidine ring bearing $X^2$ and $Y^2$ substituents; ortho position has W-C(R¹)=C=CH₂ group.

| Comp. No. | R¹ | R² | R³ | W | X² | Y² | m.p. (°C.) |
|---|---|---|---|---|---|---|---|
| 02.13 | H | H | H | O | C₂H₅ | NH—CH₃ | |
| 02.14 | H | H | H | O | OCH₃ | OCH₃ | 180–181° C. |
| 02.15 | H | H | H | O | OCH₃ | OC₂H₅ | |
| 02.16 | H | H | H | O | OCH₃ | OCHF₂ | |
| 02.17 | H | H | H | O | OCH₃ | OCH₂CF₃ | |
| 02.18 | H | H | H | O | OCH₃ | (cyclopropyl) | |
| 02.19 | H | H | H | O | OCH₃ | N(CH₃)₂ | |
| 02.20 | H | H | H | O | OCH₃ | Cl | |
| 02.21 | H | H | H | O | OCH₃ | CH₂F | |
| 02.22 | H | H | H | O | OC₂H₅ | HNCH₃ | |
| 02.23 | H | H | H | O | OCHF₂ | OCHF₂ | 139–140° C. |
| 02.24 | H | H | H | O | CH₂OCH₃ | OCH₃ | |
| 02.25 | CH₃ | H | H | O | CH₃ | CH₃ | |
| 02.26 | CH₃ | H | H | O | CH₃ | OCH₃ | 165–166° C. |
| 02.27 | CH₃ | H | H | O | OCH₃ | OCH₃ | 200–201° C. |
| 02.28 | CH₃ | H | H | O | OCH₃ | OCHF₂ | |
| 02.29 | CH₃ | H | H | O | OCHF₂ | OCHF₂ | |
| 02.30 | CH₃ | CH₃ | H | O | CH₃ | OCH₃ | |
| 02.31 | CH₃ | CH₃ | H | O | OCH₃ | OCH₃ | |
| 02.32 | H | CH₃ | H | O | OCH₃ | OCHF₂ | |
| 02.33 | H | CH₃ | H | O | OCHF₂ | OCHF₂ | |
| 02.34 | H | CH₃ | H | O | CH₃ | OCH₃ | |
| 02.35 | H | CH₃ | H | O | OCH₃ | OCH₃ | |
| 02.36 | CH₃ | H | H | O | CH₃ | OCHF₂ | |
| 02.37 | H | H | 6-NO₂ | O | OCH₃ | OCH₃ | |
| 02.38 | H | H | 5-Cl | O | OCH₃ | OCH₃ | |
| 02.39 | H | H | 5-F | O | OCH₃ | OCH₃ | |
| 02.40 | H | H | 5-CH₃ | O | CH₃ | OCH₃ | |
| 02.41 | H | H | 3-Cl | O | CH₃ | OCH₃ | |
| 02.42 | H | H | 5-Cl | O | CH³ | OCH₃ | |
| 02.43 | H | H | 6-Cl | O | CH₃ | OCH₃ | |
| 02.44 | H | H | 5-F | O | CH₃ | OCH₃ | |
| 02.45 | H | H | H | S | CH₃ | CH₃ | |
| 02.46 | H | H | H | S | CH₃ | C₂H₅ | |
| 02.47 | H | H | H | S | CH₃ | OCH₃ | |
| 02.48 | H | H | H | S | CH₃ | OC₂H₅ | |
| 02.49 | H | H | H | S | CH₃ | OCHF₂ | |
| 02.50 | H | H | H | S | CH₃ | OCH₂CF₃ | |
| 02.51 | H | H | H | S | CH₃ | (cyclopropyl) | |
| 02.52 | H | H | H | S | CH₃ | HN—CH₃ | |
| 02.53 | H | H | H | S | CH₃ | N(CH₃)₂ | |
| 02.54 | H | H | H | S | CH₂Cl | OCH₃ | |
| 02.55 | H | H | H | S | C₂H₅ | OCH₃ | |
| 02.56 | H | H | H | S | C₂H₅ | OCHF₂ | |
| 02.57 | H | H | H | S | C₂H₅ | HN—CH₃ | |
| 02.58 | H | H | H | S | OCH₃ | OCH₃ | 156–157° C. |
| 02.59 | H | H | H | S | OCH₃ | OCHF₂ | |
| 02.60 | H | H | H | S | OCH₃ | OCH₂CF₂ | |
| 02.61 | H | H | H | S | OCH₃ | (cyclopropyl) | |
| 02.62 | H | H | H | S | OCH₃ | N(CH₃)₂ | |

TABLE 02-continued $$\text{(Ib)}$$

Structure: R³-substituted phenyl with SO₂NH-C(=O)-N(R²)- linked to pyrimidine bearing X² and Y²; ortho substituent W-C(R¹)=C=CH₂

| Comp. No. | R¹ | R² | R³ | W | X² | Y² | m.p. (°C.) |
|---|---|---|---|---|---|---|---|
| 02.63 | H | H | H | S | OCH₃ | Cl | |
| 02.64 | H | H | H | S | OCH₃ | CH₂F | |
| 02.65 | H | H | H | S | OC₂H₅ | HN—CH₃ | |
| 02.66 | H | H | H | S | OCHF₂ | OCHF₂ | |
| 02.67 | CH₃ | H | H | S | CH₃ | CH₃ | |
| 02.68 | CH₃ | H | H | S | OCH₃ | OCH₃ | 168–169° C. |
| 02.69 | H | H | H | SO | CH₃ | OCH₃ | |
| 02.70 | H | H | H | SO | OCH₃ | OCH₃ | |
| 02.71 | H | H | H | SO₂ | CH₃ | OCH₃ | |
| 02.72 | H | H | H | SO₂ | OCH₃ | OCH₃ | 181–182° C. |
| 02.73 | H | H | H | SO₂ | OCHF₂ | OCHF₂ | |
| 02.74 | H | H | H | SO₂ | CH₃ | CH₃ | |
| 02.75 | H | H | H | SO₂ | CH₃ | OCHF₂ | |
| 02.76 | H | H | H | O | OC₂H₅ | OCHF₂ | |
| 02.77 | H | H | H | S | OC₂H₅ | OCHF₂ | |
| 02.78 | H | H | H | SO₂ | OCH₃ | OCHF₂ | |

TABLE 03

$$\text{(Ic)}$$

Structure: R³-substituted phenyl with SO₂NH-C(=O)-N(R²)- linked to triazine bearing X² and Y¹; ortho substituent W-C(R¹)=C=CH₂

| Comp. No. | R¹ | R² | R³ | W | X² | Y² | m.p. (°C.) |
|---|---|---|---|---|---|---|---|
| 03.01 | H | H | H | O | CH₃ | OCH₃ | 150–151° C. decomp. |
| 03.02 | H | H | H | O | CH₃ | OC₂H₅ | |
| 03.03 | H | H | H | O | CH₃ | OCH₂CF₃ | |
| 03.04 | H | H | H | O | CH₃ | CH₃ | |
| 03.05 | H | H | H | O | CH₃ | (cyclopropyl) | |
| 03.06 | H | H | H | O | OCH₃ | OCH₃ | 154–155° C. |
| 03.07 | H | H | H | O | OCH₃ | OC₂H₅ | |
| 03.08 | H | H | H | O | OCH₃ | N(CH₃)₂ | |
| 03.09 | H | H | H | O | OCH₃ | OCH₂CF₃ | |
| 03.10 | H | H | H | O | CH₂Cl | OCH₃ | |
| 03.11 | H | H | H | O | CH₂F | OCH₃ | |
| 03.12 | H | H | H | O | C₂H₅ | OCH₃ | |
| 03.13 | H | H | H | O | OC₂H₅ | HN—CH₃ | |
| 03.14 | H | H | H | O | OC₂H₅ | OC₂H₅ | |
| 03.15 | CH₃ | H | H | O | CH₃ | OCH₃ | 146–147° C. |
| 03.16 | CH₃ | H | H | O | OCH₃ | OCH₃ | 150–152° C. |
| 03.17 | CH₃ | CH₃ | H | O | CH₃ | OCH₃ | |
| 03.18 | H | H | 5-CH₃ | O | CH₃ | OCH₃ | 162–163° C. |
| 03.19 | H | H | 5-CH₃ | O | CH₃ | OCH₃ | |
| 03.20 | H | H | H | S | CH₃ | OCH₃ | 130–131° C. |
| 03.21 | H | H | H | S | OCH₃ | OCH₃ | 144–145° C. |
| 03.22 | H | H | H | S | OCH₃ | N(CH₃)₂ | |
| 03.23 | H | H | H | S | OCH₃ | OCH₂CF₃ | |
| 03.24 | H | H | H | S | CH₃ | OC₂H₅ | |
| 03.25 | H | H | H | S | C₂H₅ | OCH₃ | |
| 03.26 | H | H | H | S | OC₂H₅ | HN—CH₃ | |
| 03.27 | CH₃ | H | H | S | CH₃ | OCH₃ | 156–157° C. |
| 03.28 | CH₃ | H | H | S | OCH₃ | OCH₃ | |
| 03.29 | H | H | H | SO | CH₃ | OCH₃ | |
| 03.30 | H | H | H | SO | OCH₃ | OCH₃ | |
| 03.31 | CH₃ | H | H | SO₂ | CH₃ | OCH₃ | |
| 03.32 | CH₃ | H | H | SO₂ | OCH₃ | OCH₃ | |

03.33: Phenyl with SO₂NH-C(=O)-NH- linked to triazine bearing CH₃ and OCH₃; ortho substituent S-CH=C=C(CH₃)₂; m.p. 150–151° C.

TABLE 04

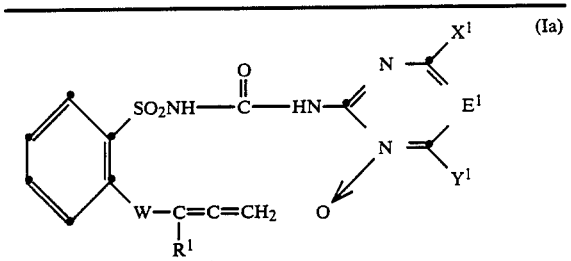

(Ia)

| Comp. No. | $R^1$ | W | $E^1$ | $X^1$ | $Y^1$ | m.p. (°C.) |
|---|---|---|---|---|---|---|
| 04.01 | H | O | CH | $CH_3$ | $OCH_3$ | |
| 04.02 | $CH_3$ | O | CH | $CH_3$ | $OCH_3$ | |
| 04.03 | H | S | CH | $CH_3$ | $OCH_3$ | |
| 04.04 | H | O | CH | $CH_3$ | $CH_3$ | |
| 04.05 | $CH_3$ | O | CH | $CH_3$ | $CH_3$ | |
| 04.06 | H | S | CH | $CH_3$ | $CH_3$ | |
| 04.07 | H | O | N | $CH_3$ | $CH_3$ | |
| 04.08 | $CH_3$ | O | N | $CH_3$ | $CH_3$ | |
| 04.09 | H | S | N | $CH_3$ | $CH_3$ | |
| 04.10 | H | O | CH | $CH_3$ | $OC_2H_5$ | |
| 04.11 | H | O | CH | $OCH_3$ | $OCH_3$ | |
| 04.12 | H | O | CH | $N(CH_3)_2$ | $OCH_3$ | |
| 04.13 | H | $SO_2$ | CH | $CH_3$ | $OCH_3$ | |
| 04.14 | H | $SO_2$ | N | $CH_3$ | $OCH_3$ | |

TABLE 05

(Ia)

| Comp. No. | $X^3$ | $Y^3$ | $Z^3$ | W | m.p. (°C.) |
|---|---|---|---|---|---|
| 05.01 | $OCH_3$ | $OCH_3$ | $CH_3$ | O | |
| 05.02 | $CH_3$ | $OCH_3$ | $CH_3$ | O | |
| 05.03 | $OCH_3$ | $CH_3$ | $CH_3$ | O | |
| 05.04 | $OCH_3$ | $OCH_3$ | Cl | O | |
| 05.05 | $CH_3$ | $OCH_3$ | Cl | O | |
| 05.06 | $OCH_3$ | $OCH_3$ | F | O | |
| 05.07 | $OCH_3$ | $OCH_3$ | $CF_3$ | O | |
| 05.08 | $OCH_3$ | $-CH_2-CH_2-CH_2-$ | | O | |
| 05.09 | $OCH_3$ | $OCH_3$ | $CH_3$ | S | |
| 05.10 | $OCH_3$ | $OCH_3$ | $OCH_3$ | $SO_2$ | |

TABLE 06

(Ie)

| Comp. No. | $X^4$ | $Y^4$ | m.p. (°C.) |
|---|---|---|---|
| 06.01 | $CH_3$ | $CH_3$ | |
| 06.02 | $CH_3$ | H | |
| 06.03 | $OCH_3$ | H | |
| 06.04 | $OCH_3$ | $OCH_3$ | |

TABLE 07

(If)

| Comp. No. | $X^5$ | $Z^5$ | m.p. (°C.) |
|---|---|---|---|
| 07.01 | $OCH_3$ | $CH_3$ | |
| 07.02 | $CH_3$ | $CH_3$ | |

TABLE 08

(Ig)

| Comp. No. | $X^6$ | $Y^6$ | $Y^{6\,1}$ | m.p. (°C.) |
|---|---|---|---|---|
| 08.01 | $OCH_3$ | $CH_3$ | H | |
| 08.02 | $OCH_3$ | H | $CH_3$ | |
| 08.03 | $CH_3$ | $CH_3$ | H | |

TABLE 09

(Ih)

| Comp. No. | $E^2$ | n | $X^7$ | m.p. (°C.) |
|---|---|---|---|---|
| 09.01 | O | 1 | $CH_3$ | |
| 09.02 | O | 1 | $OCH_3$ | |
| 09.03 | $CH_2$ | 1 | $OCH_3$ | |
| 09.04 | O | 2 | $OCH_3$ | |
| 09.05 | $CH_2$ | 2 | $OCH_3$ | |
| 09.06 | $CH_2$ | 1 | $CH_3$ | |

TABLE 10

(Ii)

| Comp. No. | $X^8$ | $Y^8$ | $Y^{8\,1}$ | m.p. (°C.) |
|---|---|---|---|---|
| 10.01 | $CH_3$ | H | $CH_3$ | |
| 10.02 | $OCH_3$ | H | $CH_3$ | |
| 10.03 | $OCH_3$ | H | H | |
| 10.04 | $CH_3$ | $CH_3$ | $CH_3$ | |
| 10.05 | $OCH_3$ | $CH_3$ | $CH_3$ | |

FORMULATION EXAMPLES

Example 2

Formulation Examples for compounds of formula I (percentages are by weight)

| (a) Wettable powders | (a) | (b) | (c) |
|---|---|---|---|
| compound of the Tables | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrates | (a) | (b) |
|---|---|---|
| compound of the Tables | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| compound of the Tables | 0.1% | 1% |
| talcum | 99.9% | — |
| kaolin | — | 99% |

Dusts which are ready for use are obtained by mixing the active ingredient with the carrier, and grinding the mixture in a suitable mill.

| (d) Extruder granulates | (a) | (b) |
|---|---|---|
| compound of the Tables | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| compound of the Tables | 3% |
| polyethylene glycol (mol. wt. 200) | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrates | (a) | (b) |
|---|---|---|
| compound of the Tables | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| compound of the Tables | 5% |
| isopropylamine | 1% |
| octylphenol polyethylene glycol ether (78 moles of ethylene oxide) | 3% |
| water | 91% |

BIOLOGICAL EXAMPLES

Example 4

Preemergence herbicidal action

Plastic pots are filled with expanded vermiculite (density: 0.135 g/cm$^3$; water-absorbing capacity: 0.565 l/l). After the non-adsorptive vermiculite has been saturated with an aqueous emulsion in deionised water which contains the test compound in a concentration of 70.8 ppm, seeds of the following plants are sown on the surface: *Nasturtium officinalis*, *Agrostis tenuis*, *Stellaria media* and *Digitaria sanguinalis*. The pots are then kept in a climatic chamber at 20° C., an illumination of about 20 klux and a relative humidity of 70%. During the germinating phase of 4 to 6 days, the pots are covered with lightpermeable material and watered with deionised water to increase the local humidity. After the 5th day, 0.5% of a commercial liquid fertiliser (Greenzit ®) is added to the water. The test is evaluated 12 days after sowing and the action on the test plants is assessed. The test compounds of formula I exhibit good to very good herbicidal activity in this test.

Pre-emergence action:

Concentration of compound emulsion: 70.8 ppm

| Plant Compound No. | Nasturtium | Stellaria | Agrostis | Digitaria |
|---|---|---|---|---|
| 2.01 | 2 | 2 | 2 | 2 |
| 2.03 | 2 | 2 | 2 | 2 |
| 2.05 | 2 | 2 | 2 | 2 |
| 2.14 | 2 | 2 | 2 | 2 |
| 2.23 | 2 | 2 | 3 | 3 |
| 2.26 | 2 | 2 | 2 | 2 |
| 2.27 | 2 | 2 | 2 | 2 |
| 2.50 | 2 | 2 | 2 | 2 |
| 2.58 | 2 | 2 | 2 | 2 |
| 2.68 | 2 | 2 | 2 | 2 |
| 2.72 | 2 | 3 | 2 | 3 |
| 3.01 | 2 | 2 | 2 | 2 |
| 3.06 | 2 | 2 | 2 | 2 |
| 3.15 | 3 | 3 | 3 | 3 |
| 3.16 | 2 | 2 | 2 | 2 |
| 3.18 | 2 | 2 | 2 | 2 |
| 3.20 | 2 | 2 | 2 | 2 |
| 3.21 | 2 | 2 | 2 | 2 |

| Plant Compound No. | Nasturtium | Stellaria | Agrostis | Digitaria |
|---|---|---|---|---|
| 3.27 | 2 | 2 | 2 | 2 |

Example 5

Growth inhibition of cereals

Summer barley (*Hordeum vulgare*) and summer rye (Secale) are sown in sterilised soil in plastic beakers in a greenhouse and watered as required. The cereal shoots are treated about 21 days after sowing with an aqueous spray mixture of a compound of formula I. The concentration corresponds to up to 100 g of active ingredient per hectare. Evaluation of the growth of the cereals is made 21 days after application. A comparison with untreated controls shows that the new growth of treated cereal plants is reduced (60–90% of the controls) and that the diameter of the stalks has in some cases increased.

Example 6

Growth inhibition of grasses

Seeds of the grasses *Lolium perenne, Poa pratensis, Festuca ovina, Dactylis glomerate* and *Cynodon dactylon* are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of formula I. The concentration of test compound corresponds to a rate of application of up to 100 g of active ingredient per hectare. The growth of the grasses is evaluated 21 days after application.

The compounds of formula I effect a reduction in new growth in the range of 10–30% in comparison with untreated control.

What is claimed is:

1. An N-phenylsulfonyl-N'-pyrimidinylurea, of formula I

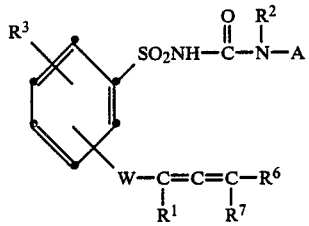

(I)

wherein
$R^1$ and $R^2$, independently of each other, are hydrogen or $C_1$-$C_2$alkyl,
$R^3$ is hydrogen, halogen, nitro, $C_1C_4$alkyl, $C_1$-$C_4$-haloalkyl, $C_1$-$C_4$-alkoxy, $C_1$-$C_4$haloalkoxy, $C_1$-$C_4$alkoxycarbonyl, $C_1$-$_4$alkylthio, $C_1$-$C_4$-alkysulfinyl, $C_1$-$C_4$alkylsulfonyl or $C_2$-$C_5$ alkoxyalkoxy or —$SO_2NR^4R^5$,
$R^4$ is hydrogen, $C_1$-$C_2$alkoxy or $C_1$-$C_4$alkyl,
$R^5$ is hydrogen, methyl or ethyl,
$R^6$ and $R^7$ are each hydrogen, methyl or ethyl,
W is oxygen, sulfur, a sulfinyl or sulfonyl bridge
A is a radical selected from

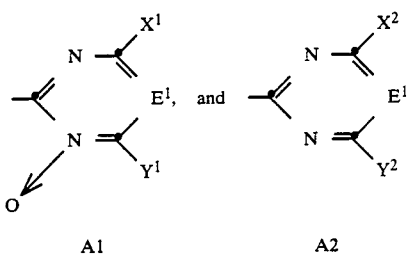

in which
$X^1$, $X^2$ and $Y^1$ are each independently halogen, $C_1$-$C_4$haloalkoxy, $C_1$-$C_4$haloalkyl, $C_1$-$C_4$alkoxy, C-$C_4$alkyl, dimethylamino, methylamino, ethylamino, amino or $C_2$-$C_4$alkoxyalkyl,
$E^1$ is the methine bridge,
$Y^2$ has the same meaning as $Y^1$ or is cyclopropyl, dimethoxymethyl, diethoxymethyl

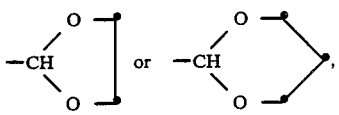

or a salt thereof.

2. An N-phenylsulfonyl-N'-pyrimidinylurea according to claim 1 of formula Ib

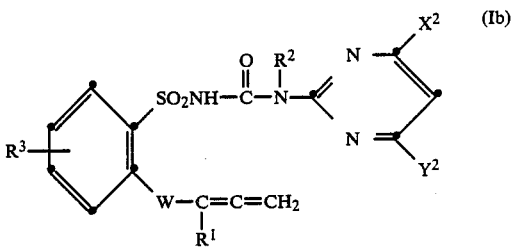

(Ib)

wherein
$R^1$ and $R^2$, independently of each other, are hydrogen or $C_1$-$C_2$alkyl,
$R^3$ is hydrogen, halogen, nitro, $C_1C_4$alkyl, $C_1$-$C_4$-haloalkyl, $C_1$-$C_4$-alkoxy, $C_1$-$C_4$haloalkoxy, $C_1$-$C_4$alkoxycarbonyl, $C_1$-$C_4$alkylthio, $C_1$-$C_4$alkylsulfinyl, $C_1$-$C_4$alkylsulfonyl or $C_2$-$C_5$alkoxyalkoxy or —$SO_2NR^4R^5$,
$R^4$ is hydrogen, $C_1$-$C_2$alkoxy or $C_1$-$C_4$alkyl,
$R^5$ is hydrogen, methyl or ethyl,
$R^6$ and $R^7$ are each hydrogen, methyl or ethyl,
W is oxygen, sulfur, a sulfinyl or sulfonyl bridge,
X is halogen, $C_1$-$C_4$alkyl, $C_1$-$C_4$haloalkyl, $C_1$-$C_4$alkoxy, $C_1$-$C_4$haloalkoxy. amino, methylamino, ethylamino, dimethylamino or $C_2$-$C_5$alkoxyalkyl and
Y has the same meanings as X or is cyclopropyl.

3. An N-phenylsulfonyl-N'-pyrimidinylurea according to claim 1 of formula Ib, wherein
$R^1$, $R^2$, $R^3$, $R^6$ and $R^7$ are hydrogen and W is oxygen and X and Y are as defined in claim 1.

4. An N-phenylsulfonyl-N'-pyrimidinylurea according to claim 1 of formula Ib, wherein
$R^1$, $R^2$, $R^3$, $R^6$ and $R^7$ are hydrogen and W is sulfur and X and Y are as defined in claim 1.

5. N-(2-Allenyloxyphenylsulfonyl)-N'-(4-methoxy-4-methylpyrimidin-2-yl)-urea according to claim 1.

6. N-(2-Allenyloxyphenylsulfonyl)-N'-(4,6-dimethoxypyrimidin-2-yl)-urea according to claim 1.

7. N-(2-Allenyloxyphenylsulfonyl)-N'-(4,6-bis-difluoromethoxypyrimidin-2-yl)-urea according to claim 1.

8. A herbicidal and plant-growth inhibiting composition which, in addition to inert carriers and/or other adjuvants, comprises a herbicidally and plant growth regulating effective amount of a phenylsulfonylurea according to claim 1, as active ingredient.

9. A method for selectively controlling weeds in crops of useful plants, which comprises applying an effective amount of a compound according to claim 1, or a composition containing said compound, to the crops or to the locus thereof.

10. A method of inhibiting plant growth, which comprises applying an effective amount of a compound according to claim 1, or a composition containing said compound, to the plants.

* * * * *